US00PP18855P2

(12) United States Plant Patent
Hurkman

(10) Patent No.: US PP18,855 P2
(45) Date of Patent: May 27, 2008

(54) **NEW GUINEA *IMPATIENS* PLANT NAMED 'BALCELSANGI'**

(50) Latin Name: *Impatiens hawkeri*
Varietal Denomination: Balcelsangi

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 67 days.

(21) Appl. No.: 11/602,864

(22) Filed: Nov. 21, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Annette H. Para
(74) *Attorney, Agent, or Firm*—Audrey Charles

(57) ABSTRACT

A new and distinct cultivar of New Guinea *Impatiens* plant named 'Balcelsangi', characterized by its single type dark magenta-colored flowers, medium green-colored foliage; and vigorous, upright-mounded growth habit.

1 Drawing Sheet

Latin name of genus and species of plant claimed: *Impatiens hawkeri.*
Variety denomination: 'Balcelsangi'.

BACKGROUND OF THE INVENTION

The present invention relates to a new and distinct cultivar of New Guinea *Impatiens* plant botanically known as *Impatiens hawkeri* and hereinafter referred to by the cultivar name 'Balcelsangi'.

The new cultivar originated in a controlled breeding program in Arroyo Grande, Calif. during June 2003. The objective of the breeding program was the development of New Guinea *Impatiens* cultivars with numerous large flowers, attractive flower coloration, and a freely basal branching growth habit.

The new New Guinea *Impatiens* cultivar is the result of cross-pollination. The female (seed) parent of the new cultivar is the proprietary *Impatiens hawkeri* breeding selection designated 7851, not patented, characterized by its single type dark burgundy-colored flowers, medium green-colored foliage, and upright growth habit. The male (pollen) parent of the new cultivar is the proprietary *Impatiens hawkeri* breeding selection designated 3312-1, not patented, characterized by its single type medium purple-colored flowers, medium green-colored foliage, and upright-mounded growth habit. The new cultivar was discovered and selected as a single flowering plant within the progeny of the above stated cross-pollination during December 2003 in a controlled environment at Arroyo Grande, Calif.

Asexual reproduction of the new cultivar by terminal stem cuttings since December 2003 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcelsangi' as a new and distinct cultivar of New Guinea *Impatiens* plant:

1. Single type dark magenta-colored flowers;
2. Medium green-colored foliage; and
3. Vigorous, upright-mounded growth habit.

Plants of the new cultivar differ from plants of the female parent primarily in flower color and from plants of the male parent primarily in flower color.

Of the many commercially available New Guinea *Impatiens* cultivars known to the inventor, the most similar in comparison to the new cultivar is Celebration Sangria 'Balcelsan', U.S. Plant Pat. No. 11,623. However, in side by side comparisons, plants of the new cultivar differ from plants of 'Balcelsan' in the following characteristics:

1. Plants of the new cultivar have a flower color different from plants of 'Balcelsan'; and
2. Plants of the new cultivar have a foliage color different from plants of 'Balcelsan'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelsangi'. The plants were grown in 4.5 inch pots for 11 weeks in a greenhouse at West Chicago, Ill.

DETAILED BOTANICAL DESCRIPTION

Figure 1:
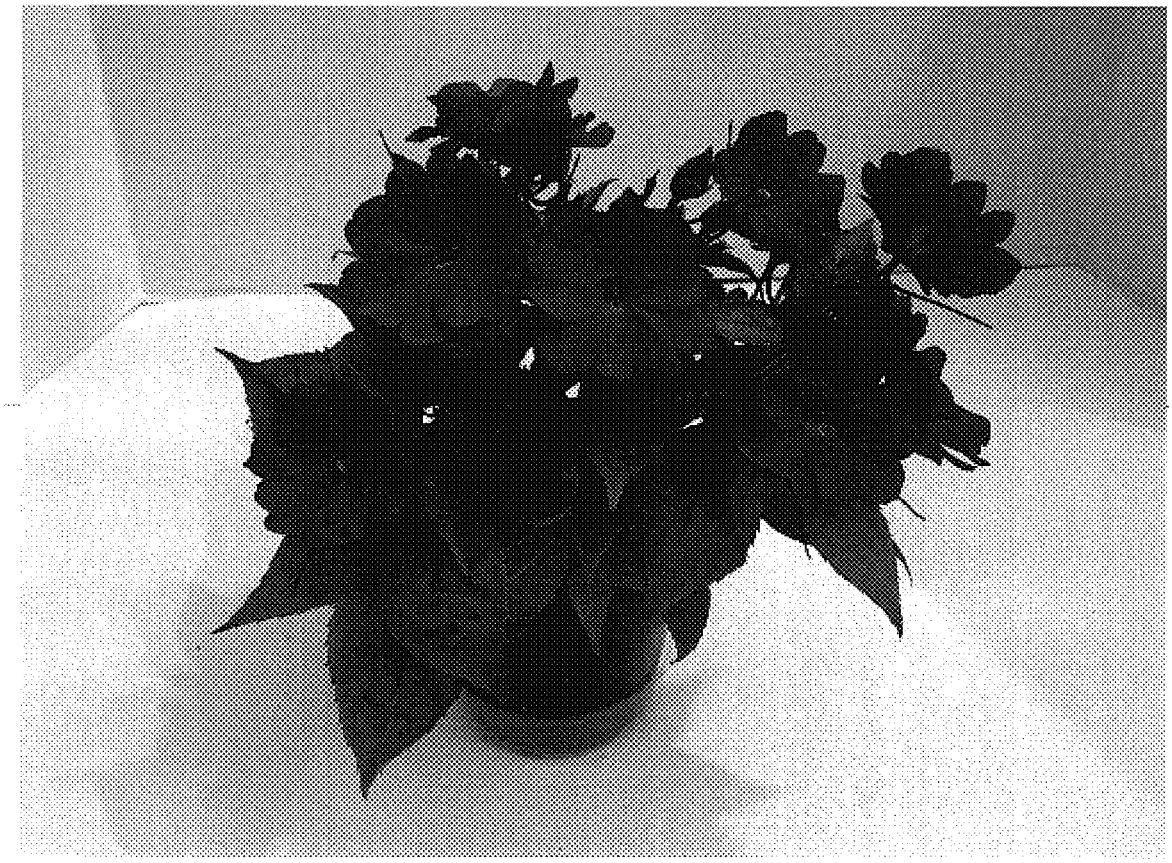
FIG. 1 illustrates a side view of the overall growth and flowering habit of 'Balcelsangi'.
Figure 2:
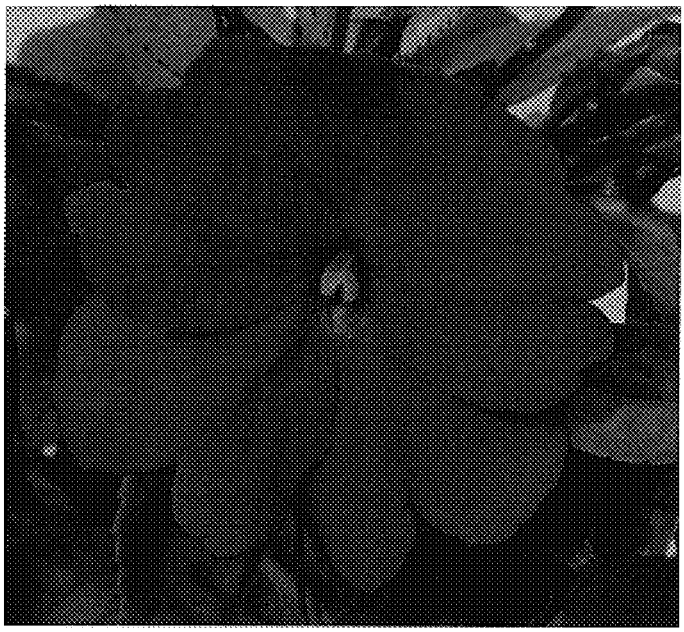
FIG. 2 illustrates a close-up view of an individual flower of 'Balcelsangi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 28, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens hawkeri* cultivar Balcelsangi.

Parentage:

*Female parent.*—*Impatiens hawkeri* breeding selection designated 7851.

*Male parent.*—*Impatiens hawkeri* breeding selection designated 3312-1.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 7 to 9 weeks from a rooted cutting.

*Growth habit and general appearance.*—Vigorous, upright-mounded.

*Size.*—Height from soil level to top of plant plane: Approximately 14.8 cm. Width: Approximately 25.8 cm.

*Branching habit.*—Freely basal branching. Quantity of main branches per plant: Approximately 5.

*Branch.*—Strength: Strong. Length: Approximately 10.6 cm. Diameter: Approximately 4.6 mm. Length of central internode: Approximately 3.4 cm. Texture: Glabrous. Color of young stem: 144B with overlay of 185A. Color of mature stem: 144B with overlay of 185A at node region.

Foliage description:

*General description.*—Quantity of leaves per main branch: Approximately 8. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 10.9 cm. Width of mature leaf at center of stem: Approximately 4.5 cm. Texture of upper surface: Glabrous. Texture of lower surface: Glabrous with sparsely pubescent midvein. Color of upper surface of young foliage: Closest to 137B with venation of 137B and an overlay on midvein of 185B that fades towards leaf apex. Color of lower surface of young and mature foliage: 138B with venation of 138B with an overlay of 185C. Color of upper surface of mature foliage: 137A with venation of 137B and an overlay on midvein of 185B that fades towards leaf apex.

*Petiole.*—Length: Approximately 1.0 cm. Diameter: Approximately 3.0 mm. Texture: Glabrous. Color: 138B with an overlay of 185C.

Flowering description:

*Flowering habit.*—'Balcelsangi' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 6. Fragrance: None.

*Bud.*—Rate of opening: Generally takes 3 to 4 days for bud to progress from first color to fully open flower. Quantity showing color per plant: Approximately 4.

*Bud just before opening.*—Shape: Ovoid. Length: Approximately 2.0 cm. Diameter: Approximately 1.4 cm. Color: Darker than N74A.

*Corolla.*—Shape: Round, cupped when first open with petals turning downward with age. Width: Approximately 6.7 cm. Depth: Approximately 1.1 cm. Borne: Above and below foliage.

*Petals.*—Quantity: 5. Shape: Obovate. Aspect: Flat. Appearance: Iridescent. Margin: Entire. Apex: Emarginate. Base of upper petal: Truncate. Base of lateral and lower petals: Attenuate. Length of upper petal: Approximately 2.9 cm. Width of upper petal: Approximately 4.6 cm. Length of lateral petals: Approximately 3.2 cm. Width of lateral petals: Approximately 2.9 cm. Length of lower petals: Approximately 3.4 cm. Width of lower petals: Approximately 3.5 cm. Texture of upper and lower surfaces: Glabrous. Color of upper surface when first open: More blue than 61A. Color of lower surface when first open: 61C. Color of upper surface when fully open: Darker and more red than N74A with a central eye of 60A. Color of lower surface when fully open: N74B.

*Spur.*—Quantity: 1 per flower. Length: Approximately 5.7 cm. Diameter at tip: Approximately 1.0 mm. Diameter at base: Approximately 3.0 mm. Texture: Glabrous. Color: 187C darkening to 187B toward tip of 145C.

*Peduncle.*—Strength: Strong. Aspect: Acute angle to stem. Length: Approximately 5.2 cm. Diameter: Approximately 2.0 mm. Texture: Glabrous. Color: 144C with an overlay of 185B.

*Sepals.*—Quantity per flower: 4, with one fused to base of upper petal. Shape of lateral and lower sepals: Ovate. Apex of all sepals: Acuminate. Length of lateral sepals: Approximately 1.5 cm. Width of lateral sepals: Approximately 6.0 mm. Length of lower sepal: Approximately 1.8 cm. Width of lower sepal: Approximately 1.4 cm. Texture of upper and lower surfaces of all sepals: Glabrous. Color of lateral sepals: 185A and tip of 144B. Color of lower sepal: Closest to N155B with an overlay of 186C and tip of 144B.

*Reproductive organs.*—Androecium: Stamen quantity: 5 per flower, fused around pistil at apex. Anther shape: Hooded. Anther length: Approximately 3.0 mm. Anther color: 160D at apex transitioning to 61C toward filament. Filament color: 61A. Pollen amount: Abundant. Pollen color: 155D. Gynoecium: Pistil quantity: 1 per flower. Pistil length: Approximately 6.0 mm. Stigma shape: 5-pointed star. Stigma color: Colorless, transparent. Style color: 144B. Ovary texture: Glabrous. Ovary color: 144B.

Seed and fruit production: Neither seed nor fruit production has been observed.

Disease and pest resistance: Resistance to pathogens and pests common to New Guinea New Guinea *Impatiens* has not been observed.

What is claimed is:

1. A new and distinct cultivar of New Guinea *Impatiens* plant named 'Balcelsangi', substantially as herein shown and described.

* * * * *